United States Patent [19]
O'Doherty

[11] 3,989,840
[45] Nov. 2, 1976

[54] CONTROL OF ANIMAL PARASITES WITH RING-SUBSTITUTED N-(2,2-DIFLUOROALKANOYL)-O-PHENYLENEDIAMINES

[75] Inventor: George Oliver Plunkett O'Doherty, Greenfield, Ind.

[73] Assignee: Eli Lilly and Company, Indianapolis, Ind.

[22] Filed: July 18, 1975

[21] Appl. No.: 597,862

[52] U.S. Cl. .................................. 424/300; 424/285; 424/324; 424/330
[51] Int. Cl.² ................... A61K 31/27; A61K 31/34; A61K 31/165
[58] Field of Search ............ 424/324, 285, 300, 330

[56] References Cited
OTHER PUBLICATIONS

Berberian et al.,–Chem. Abst., vol. 56, (1962), p. 6604a.

*Primary Examiner*—Sam Rosen
*Attorney, Agent, or Firm*—Karen L. Searle; Everet F. Smith

[57] ABSTRACT

A class of substituted o-phenylenediamines are useful parasiticides for the systemic control of insects and acarina which feed on tissues of animals. The compounds, which control both bloodsucking parasites and flesh-eating parasites, are characterized by a single nitro substituent on the benzene ring, and a single fluoroalkyl or chlorodifluoroalkyl substituent on the benzene ring.

20 Claims, No Drawings

CONTROL OF ANIMAL PARASITES WITH RING-SUBSTITUTED N-(2,2-DIFLUOROALKANOYL)-O-PHENYLENEDIAMINES

BACKGROUND OF THE INVENTION

The control of animal parasites is one of the oldest and most important problems of the animal husbandry industry. Many types of parasites afflict virtually all species of animals. Most animals are afflicted by free-flying parasites such as flies, crawling ectoparasites such as lice and mites, burrowing parasites such as bots and grubs, and by microscopic endoparasites such as coccidia, as well as by larger endoparasites such as worms. Thus, the control of parasites even in a single host species is a complex and many-sided problem.

The insect and acarina parasites which consume living tissues of a host animal are particularly harmful. The group includes parasites of all the economic animals, including ruminant and monogastric mammals and poultry, and of companion animals such as dogs as well.

Many methods of control of such parasites have been tried. The screwworm has been practically eradicated in Florida by the release of great numbers of sterile male blowflies. The method obviously is applicable only to an easily isolated area. The free-flying insects are usually controlled by routine methods such as air-dispersed and contact insecticides and fly traps. The skin-inhabiting, crawling parasites are usually controlled by dipping, drenching, or spraying the animals with appropriate parasiticides.

Some progress has been made in the systemic control of some parasites, particularly those which burrow in or migrate through the host animal. Systemic control of animal parasites is accomplished by absorbing a parasiticide in the bloodstream or other tissues of the host animal. Parasites which eat or come into contact with the parasiticide-containing tissue are killed, either by ingestion or contact. A few phosphate, phophoramidate, and phosphorothioate insecticides and acaricides have been found to be sufficiently nontoxic to be used systemically in animals.

The field of o-phenylenediamine chemistry has produced many patents. For example, Rumanowski, U.S. Pat. No. 3,557,211, discloses N,N'-bis(acetyl)-o-phenylenediamines which are useful for the control of plants, insects and fungi.

SUMMARY

This invention provides to the art a new method of killing by ingestion insect and acarina parasites which consume living tissues of a host animal which comprises orally or percutaneously administering to the host animal a parasiticidally-effective amount of a compound of the formula

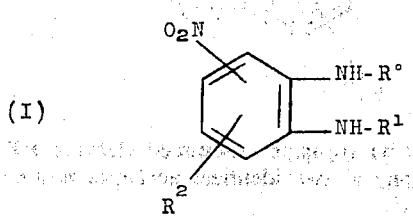

(I)

wherein
$R^°$ is a 2,2-difluoroalkanoyl radical of the formula

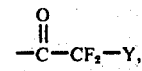

in which Y is hydrogen, chlorine, fluorine, difluoromethyl, perfluoroalkyl of $C_1$–$C_6$, or a radical of the formula

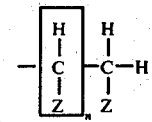

in which each Z independently is hydrogen or halogen, and $n$ is 0 or 1;
$R^1$ is $R^°$, hydrogen, a radical of the formula

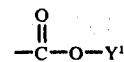

in which $Y^1$ is $C_1$–$C_4$ alkyl or phenyl, $C_1$–$C_8$ alkanoyl, benzoyl, furoyl, naphthoyl, or substituted benzoyl of the formula

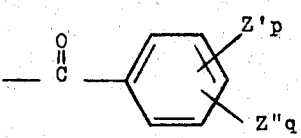

in which each $Z'$ independently is halo or nitro, $Z''$ is $C_1$–$C_4$ alkyl or $C_1$–$C_4$ alkoxy, $p$ is 0, 1, or 2, $q$ is 0 or 1, and the sum of $p$ and $q$ is 1–3;
$R^2$ is trifluoromethyl, difluoromethyl, or chlorodifluoromethyl, and the nitro group and $R^2$ are meta to one another; and
subject to the further limitation that where $R^1$ is hydrogen, the ring position ortho to the —NH—$R^1$ group bears one of the designated nitro or $R^2$ moieties.

DESCRIPTION OF THE PREFERRED EMBODIMENT

A preferred group of compounds which are useful in my method are the compounds of formula I wherein $R^1$ is other than $R^°$ or $C_1$–$C_8$ alkanoyl.

DESCRIPTION OF THE ESPECIALLY PREFERRED EMBODIMENT

An especially preferred group of compounds which are particularly useful in my method have the formula

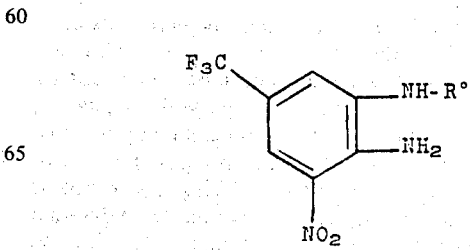

wherein R° is defined as before.

The general chemical terms in the above generic formulae are used in the sense in which they are usually understood in organic chemistry. The following specific examples of substituents referred to by the general chemical terms are presented to assure clarity.

$C_1-C_6$ alkyl, $C_1-C_4$ alkyl, and $C_1-C_4$ alkoxy, refer to substituents such as methyl, ethyl, isopropyl, isobutyl, hexyl, 2-pentyl, t-butyl, methoxy, propoxy, and 3-hexyl.

$C_1-C_8$ alkanoyl refers to substituents such as formyl, acetyl, propionyl, butyryl, isobutyryl, and octanoyl.

The following specific compounds are presented to assure that those skilled in the organic chemical and parasitological arts understand the scope of my invention.

$N^1$-trifluoroacetyl-3'-nitro-5'-trifluoromethyl-o-phenylenediamine $N^1$-(2,2,3,3-tetrafluoropropionyl)-3'-nitro-5'-trifluoromethyl-o-phenylenediamine $N^1$-trifluoroacetyl-3'-trifluoromethyl-5'-nitro-o-phenylenediamine $N^1$-chlorodifluoroacetyl-3'-nitro-5'-trifluoromethyl-o-phenylenediamine $N^1$-trifluoroacetyl-$N^2$-benzoyl-6'-nitro-4'-trifluoromethyl-o-phenylenediamine $N^1$-trifluoroacetyl-$N^2$-naphthoyl-6'-nitro-4'-trifluoromethyl-o-phenylenediamine $N^1$-trifluoroacetyl-$N^2$-(p-n-butoxybenzoyl)-4'-trifluoromethyl-6'-nitro-o-phenylenediamine $N^1$-trifluoroacetyl-$N^2$-(p-nitrobenzoyl)-4'-trifluoromethyl-6'-nitro-o-phenylenediamine $N^1$-heptafluorobutyryl-3'-nitro-5'-trifluoromethyl-o-phenylenediamine $N^1$-pentafluoropropionyl-3'-nitro-5'-trifluoromethyl-o-phenylenediamine $N^1$-trifluoroacetyl-$N^2$-acetyl-6'-nitro-4'-trifluoromethyl-o-phenylenediamine $N^1$-trifluoroacetyl-$N^2$-isobutyryl-6'-nitro-4'-trifluoromethyl-o-phenylenediamine $N^1$-trifluoroacetyl-$N^2$-methoxycarbonyl-4'-trifluoromethyl-6'-nitro-o-phenylenediamine $N^1$-pentadecafluorooctanoyl-3'-nitro-5'-trifluoromethyl-o-phenylenediamine $N^1$-(2,2,3,3-tetrafluoropropionyl)-$N^2$-methoxycarbonyl-6'-nitro-4'-trifluoromethyl-o-phenylenediamine $N^1$-pentafluoropropionyl-3'-nitro-5'-trifluoromethyl-o-phenylenediamine $N^1$-difluoroacetyl-$N^2$-phenoxycarbonyl-4'-nitro-6'-trifluoromethyl-o-phenylenediamine $N^1$-(2,2-difluoropropionyl)-$N^2$-furoyl-4'-nitro-6'-difluoromethyl-o-phenylenediamine $N^1$-(2,2,3-trifluoropropionyl)-$N^2$-(p-chlorobenzoyl)-3'-nitro-5'-chlorodifluoromethyl-o-phenylenediamine $N^1$-(2,2-difluorobutyryl)-$N^2$-(p-methoxybenzoyl)-3'-nitro-5'-trifluoromethyl-o-phenylenediamine $N^1$-(2,2,3,4-tetrafluorobutyryl)-$N^2$-(2,6-dichloro-4-methylbenzoyl)-5'-nitro-3'-trifluoromethyl-o-phenylenediamine.

Organic chemists are now aware of the synthetic methods which are used to make the o-phenylenediamines of my method. Some explanation of the synthetic methods and a few specific examples will be given, however, to assure that all may obtain the compounds.

The compounds of formula I are prepared by introduction of the characteristic 2,2-difluoroalkanoyl group into the appropriate corresponding diamine starting material. Introduction of this group can be achieved by any of numerous available acylation reactions, employing any of several types of acylating agents of the formula

(III)

wherein Y is defined as hereinbefore, or the active derivative thereof. The identity of the acylating agent is not critical; suitable acylating agents include the 2,2-difluoroalkanoyl halides:

(IV)

and the 2,2-difluoroalkanoic anhydrides:

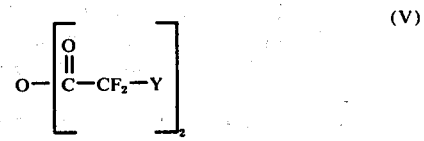
(V)

wherein Y is defined as hereinbefore. The diamine starting materials with which the acylation reaction is carried out will vary.

Thus, a process for the preparation of the compounds of formula I comprises acylating a compound of the formulae:

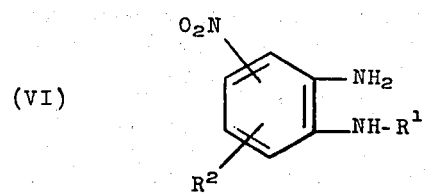
(VI)

wherein the various symbols are defined as hereinbefore, with an acylating agent of the formula

(III)

wherein Y is defined as above or the active derivative thereof.

In the instance of the compounds of formula I wherein $R^1$ is hydrogen, the starting diamine is a compound of the formula:

(VII) 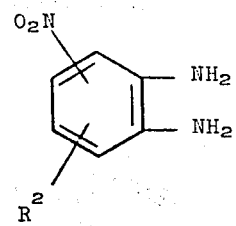

and either one acyl group is introduced (leaving $R^1$ equal to hydrogen) or two identical acyl groups are introduced ($R°$ is

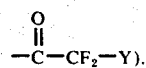

Where, on the other hand, $R^1$ is any other moiety than hydrogen, the appropriate diamine starting material is a compound already bearing the desired $R^1$ moiety of the formula:

(VIII) 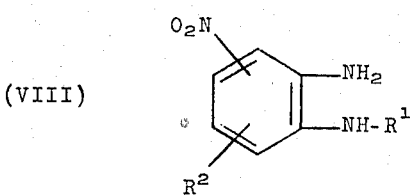

wherein the symbols are defined as hereinbefore, and the characteristic $R°$ group is similarly introduced by acylation.

While the synthetic routes described above are convenient and preferred, yet other routes can be utilized. Thus, for example, in the instance where $R^1$ is an acyl group, the $R^1$ group is conveniently introduced in some instances after the $R°$ has already been introduced. However, because of the activating effect on acylation of the alpha fluorine atoms, it is generally preferred that groups other than the 2,2-difluoroalkanoyl moiety already be present when this group is introduced.

The preparation of amides by the acylating of corresponding amines with various acylating agents is a known synthetic method. The present preparations are conducted in accordance with the known procedures for effecting this method. Thus, where the acylating agent is an anhydride, the reaction is conveniently conducted at room temperature; solvent, which can be excess anhydride, except in the case of amides where $R^1$ is hydrogen, can be utilized. Where an acyl halide is employed as acylating agent, the reaction is preferably conducted in the presence of a hydrogen halide acceptor and preferably in the presence of an inert solvent, and the reaction mixture is preferably cooled, such as to temperatures of 0°–10° C. In the case of either acylating agent, the product is separated in conventional procedures, and can be purified if desired, likewise in conventional procedures.

For the sake of uniformity, starting materials and products herein are named, where possible, as o-phenylenediamines. In accordance with common nomenclature practice, the identification of various substituent positions is as follows:

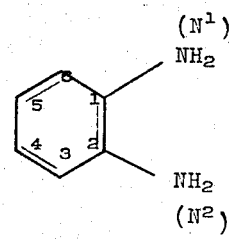

where either nitrogen atom bears an alkanoyl or other ($R°$, $R^1$) substituent, the ring position numbers are identified as prime numbers to distinguish them from numbers of positions on the $R°$ or $R^1$ substituent.

In the foregoing definition of the compounds of formula I, as employed in the present specification and claims, each of the terms "halo" and "halogen," when unqualified but as used both alone and in the composite term "halogenated alkanoyl," designates bromine, chlorine, fluorine, or iodine, only.

An essential and distinguishing structural feature of the compounds of formula I is the 2,2-difluoroalkanoyl-radical ($R°$); representative of such radicals include the following:

difluoroacetyl
trifluoroacetyl
chlorodifluoroacetyl
pentafluoropropionyl
heptafluorobutyryl
nonafluorovaleryl
2,2,3,3-tetrafluoropropionyl
undecafluorohexanoyl
tridecafluoroheptanoyl
pentadecafluorooctanoyl
2,2-difluoropropionyl
2,2-difluorobutyryl
2,2-difluoro-3-bromopropionyl
2,2-difluoro-3-chloropropionyl
2,2-difluoro-3,4-dichlorobutyryl
2,2-difluoro-4-bromobutyryl
2,2,3-trifluoropropionyl
2,2,3-trifluorobutyryl
2,2,3,4-tetrafluorobutyryl
2,2-difluoro-3-bromo-4-chlorobutyryl Preferred $R°$ groups are trifluoroacetyl, difluoroacetyl, chlorodifluoroacetyl, and 2,2,3,3-tetrafluoropropionyl.

The starting materials to be employed in accordance with the present invention are prepared by known procedures, and some of them are commercially available. Those starting materials which are of the formula (IX) 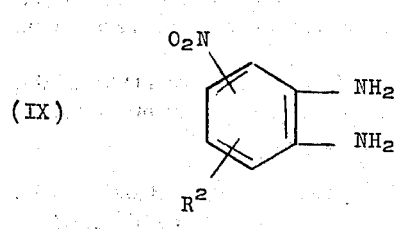

are prepared by a plurality of synthetic steps as are necessary to introduce the required moieties. Most conveniently, one of the $NH_2$ groups is introduced by conversion of a halo group. Also, the amino group or groups can be introduced by nitration and subsequent reduction. These various synthetic steps are generally and most conveniently carried out with starting materials already bearing the requisite $R^2$ and nitro moieties. However, it is sometimes preferred that these substituents be introduced simultaneously with the synthetic steps leading to the introduction of the amino group.

Those of the compounds of formula I wherein $R^1$ is a moiety other than hydrogen generally are prepared from diamine starting materials already bearing the requisite $R^1$ moiety. These starting materials are themselves prepared from the corresponding diamine starting materials described above, by reaction with an appropriate acyl halide or, in the instance of $R^1$ representing $$-\overset{O}{\underset{\|}{C}}-O-Y'$$

with an appropriate loweralkyl or phenyl haloformate. Alternately, however, these starting materials can be prepared from o-nitroanilines:

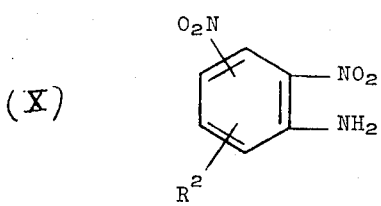

by acylation and subsequent reduction, both in procedures well known in the prior art.

The examples immediately below show the synthesis of typical exemplary compounds. Organic chemists, guided by the above general teaching as well as the common skill of the chemical art, can use the methods of the examples below to prepare all the o-phenylenediamines useful in my method.

EXAMPLE 1

Finely-ground 3-trifluoromethyl-5-nitro-o-phenylenediamine (2.2 grams), triethylamine (1.0 ml.), and chloroform (10 milliliters) were mixed and stirred while trifluoroacetic anhydride (2–3 milliliters in chloroform [20 milliliters]) was added. The addition was carried out portionwise over a period of 20 minutes at room temperature. The resulting reaction mixture was filtered to separate the desired $N^1$-trifluoroacetyl-3'-trifluoromethyl-5'-nitro-o-phenylenediamine product which was recrystallized from benzene, m.p., 201°–02° C.

Analysis, Calc. for $C_9H_5F_6N_3O_3$; (percent): C, 34.08; H, 1.58; N, 13.24. Found: C, 34.24; H, 1.60; N, 13.24.

EXAMPLE 2

3-Nitro-5-trifluoromethyl-o-phenylenediamine (5.0 grams) was mixed with 15 milliliters of pyridine and the mixture was cooled to 0° C. Chlorodifluoroacetyl chloride (3 milliliters) was then added with stirring over a period of 20 minutes. After standing at 20° C. for about 1.5 hours, the reaction mixture was mixed with 150 grams of ice and 20 milliliters of hydrochloric acid, which resulted in the precipitation of the desired $N^1$-chlorodifluoroacetyl-3'-nitro-5'-trifluoromethyl-o-phenylenediamine product. It was separated by filtration and recrystallized from benzene, m.p. 186°–88° C.

EXAMPLE 3

$N^2$-Benzoyl-6-nitro-4-trifluoromethyl-o-phenylenediamine (3.2 grams) and excess trifluoroacetic anhydride were mixed and allowed to stand overnight. Excess trifluoroacetic anhydride and the corresponding by-product acid were evaporated under vacuum to separate the desired $N^1$-trifluoroacetyl-$N^2$-benzoyl-6'-nitro-4'-trifluoromethyl-o-phenylenediamine product, which, after recrystallization from benzene, melted at 193°–95° C.

EXAMPLE 4

Other compounds representative of the present invention are readily prepared in the procedures of the foregoing teachings and examples, using analogous starting materials. Such compounds include the following:

$N^1$-Trifluoroacetyl-3'-nitro-5'-trifluoromethyl-o-phenylenediamine, m.p., 194°–95° C., prepared by reacting trifluoroacetic anhydride with 3-nitro-5-trifluoromethyl-o-phenylenediamine.

$N^1$-(2,2-Difluoro-3-bromopropionyl)-$N^2$-(2-chloro-4-tert.-butylbenzoyl)-3'-nitro-5'-trifluoromethylo-phenylenediamine, prepared by reacting 2,2-difluoro-3-bromopropionyl chloride with $N^2$-(2-chloro-4-tert.-butylbenzoyl)-3-nitro-5-trifluoromethyl-o-phenylenediamine.

$N^1$-Chlorodifluoroacetyl-$N^2$-(phenoxycarbonyl)-3'-nitro-5'-difluoromethyl-o-phenylenediamine, prepared by reacting chlorodifluoroacetic anhydride with $N^2$-(phenxoycarbonyl)-3-nitro-5-difluoromethyl-o-phenylenediamine.

$N^1$-Trifluoroacetyl-$N^2$-naphthoyl-6'-nitro-4'-trifluoromethyl-o-phenylenediamine, m.p., 200°–04° C., prepared by reacting trifluoroacetic anhydride with $N^2$-naphthoyl-5-nitro-4-trifluoromethyl-o-phenylenediamine.

$N^1$-Trifluoroacetyl-$N^2$-(p-n-butoxybenzoyl)-4'-trifluoromethyl-6'-nitro-o-phenylenediamine, m.p., 172°–74° C.

$N^1$-Trifluoroacetyl-$N^2$-(p-nitrobenzoyl)-4'-trifluoromethyl-6'-nitro-o-phenylenediamine, m.p., 210°–12° C.

$N^1$-Heptafluorobutyryl-3'-nitro-5'-trifluoromethyl-o-phenylenediamine, m.p., 118°–20° C.

$N^1$-Pentafluoropropionyl-3'-nitro-5'-trifluoromethyl-o-phenylenediamine, m.p., 161°–63° C.

$N^1$-Trifluoroacetyl-$N^2$-methoxycarbonyl-4'-trifluoromethyl-6'-nitro-o-phenylenediamine, m.p., 129°–30° C.

$N^1$-Pentadecafluorooctanoyl-3'-nitro-5'-trifluoromethyl-o-phenylenediamine, m.p., 111°–13° C.

$N^1$-Trifluoroacetyl-$N^2$-benzoyl-3'-trifluoromethyl-5'-nitro-o-phenylenediamine.

$N^1$-Trifluoroacetyl-$N^2$-naphthoyl-4'-trifluoromethyl-6'-nitro-o-phenylenediamine.

$N^1$-Difluoroacetyl-$N^2$-furoyl-3'-nitro-5'-trifluoromethyl-o-phenylenediamine.

$N^1$-(2,2,3,3-Tetrafluoropropionyl)-$N^2$-methoxycarbonyl-6'-nitro-4'-trifluoromethyl-o-phenylenediamine, m.p., 129°–30° C.

$N^1$-(2,2,3,3-Tetrafluoropropionyl)-3'-nitro-5'-trifluoromethyl-o-phenylenediamine.

$N^1$-(2,2,3,3-Tetrafluoropropionyl)-3'-nitro-5'-trifluoromethyl-o-phenylenediamine, m.p., 144°–45° C., prepared by reacting 2,2,3,3-tetrafluoropropionyl bromide with 3-nitro-5-trifluoromethyl-o-phenylenediamine.

$N^1$-Pentafluoropropionyl-3'-nitro-5'-trifluoromethyl-o-phenylenediamine, m.p., 161°–63° C., prepared by reacting pentafluoropropionyl bromide with 3-nitro-5-trifluoromethyl-o-phenylenediamine.

The method of parasite control which I have invented is of the systemic type. The compounds of formula I are useful parasiticides for the systemic control of insects and acarina which feed on living tissues of animals. These compounds have the ability to permeate the living tissues of a host animal to which one of the compounds is administered. Insect and acarina parasites which consume blood or other living tissues of the host animal ingest the compounds with which the tissue is permeated, and are thereby killed. It is probable that the blood is the agency through which the compound is dispersed through the host animal, but parasites such as screwworms, which do not suck blood, are killed by these compounds, indicating that the compounds permeate other tissues as well as blood.

Some parasites, such as most ticks, feed on living tissues of the host animal during most of the parasite's life. Other parasites, such as screwworms, feed on the host only in the larval stage. A third group of parasites, such as the bloodsucking flies, feed on animal hosts only in the adult stage. Administration of the compounds of formula I to host animals kills parasites which feed on the living tissues of the animals, no matter what the life stage of the feeding parasite.

All the species of insect and acarina parasites which feed on the living tissues of animals are killed by the compounds of formula I. The parasites which suck the host animal's blood, those which burrow into and feed on the animal's tissue, and those, like the larvae of the bot flies, which enter a natural orifice of the host, attach to the mucous membranes, and feed therefrom are all equally effectively killed. For the sake of clarity, a number of specific parasites of various host animals which are controlled by using these compounds will be mentioned. The parasitic life stage and the means by which it infests the host animal are given for each parasite.

Parasites of Horses
   horsefly, adult, bloodsucking
   stable fly, adult, bloodsucking
   black fly, adult, bloodsucking
   horse sucking louse, immature, adult, bloodsucking
   mange mite, nymph, adult, skin-burrowing
   scab mite, adult, skin-eating
   common horse bot fly, larva, migrating in alimentary canal
   chin fly, larva, migrating in alimentary canal
   nose bot fly, larva, migrating in alimentary canal
Parasites of Bovines
   horn fly, adult, bloodsucking
   cattle biting louse, adult, skin-eating
   cattle bloodsucking louse, nymph, adult, bloodsucking
   tsetse fly, adult, bloodsucking
   stable fly, adult, bloodsucking
   horse fly, adult, bloodsucking
   cattle follicle mite, adult, skin-burrowing
   cattle tick, larva, nymph, adult, bloodsucking
   ear tick, nymph, bloodsucking
   Gulf Coast tick, adult, bloodsucking
   Rocky Mountain spotted-fever tick, adult, bloodsucking
   lone star tick, adult, bloodsucking
   heel fly, larva, migrating through the body
   bomb fly, larva, migrating through the body
   blowfly, larva, infesting wounds
   assassin bug, bloodsucking
Parasites of Swine
   hog louse, nymph, adult, bloodsucking
   chigoe flea, adult, bloodsucking
Parasites of Sheep and Goats
   bloodsucking body louse, adult, bloodsucking
   bloodsucking foot louse, adult, bloodsucking
   sheep ked, adult, bloodsucking
   sheep scab mite, nymph, adult, skin-eating
   nose fly, larva, migrating in the sinuses
   greenbottle fly, larva, infesting wounds
   black blowfly, larva, infesting wounds
   secondary screwworm, larva, infesting wounds
Parasites of Poultry
   bed bug, nymph, adult, bloodsucking
   Southern chicken flea, adult, bloodsucking
   fowl tick, nymph, adult, bloodsucking -continued
   chicken mite, nymph, adult, bloodsucking
   scaly-leg mite, adult, skin-burrowing
   depluming mite, adult, skin-burrowing
Parasites of Dogs
   horse fly, adult, bloodsucking
   stable fly, adult, bloodsucking
   mange mite, nymph, adult, skin-burrowing
   dog follicle mite, adult, burrowing in hair follicles
   flea, adult, bloodsucking It will be understood that the parasites mentioned above are not confined to the single host animal with which each is here identified. Most parasites inhabit various hosts, although each parasite has a favorite host. For example, the mange mite attacks at least horses, hogs, mules, humans, dogs, cats, foxes, rabbits, sheep, and cattle. Horseflies freely attack horses, mules, cattle, hogs, dogs, and most other animals. Use of the compounds of formula I kills parasites of the types described above growing in the host animals mentioned above, and in other host animals as well. For example, these compounds are effective in cats, goats, camels, and zoo animals.

The host animals in which these compounds are preferably used are dogs, bovines, sheep, or horses for the control of ticks, fleas, flies, or screwworms.

The time, manner, and rates at which the compounds are effectively administered may be varied over a wide range. Detailed explanation of the ways in which these compounds are used will be given hereinbelow.

The compounds are administered to the animals at rates from about 1 to about 100 mg./kg. The best rate for killing a given parasite infesting a given animal must be determined individually, but it will be found that in most cases the optimum rate is within the preferred range of from about 2.5 to 50 mg./kg. The optimum rate for a given instance depends on such factors as the health of the animal to be treated, the susceptibility of the parasite of primary concern, the expense which can be borne by the animal, and the degree of control desired. Lower rates are safer for the host animal, less expensive, and often easier to administer, but are likely to give incomplete or minimum control of the parasite so that reinfestation may occur. On the other hand, higher rates of administration give more complete control of the parasites, but are more expensive and may impose a stress on the treated animals.

The compounds of formula I are effective when administered at any time of year to animals of any age. It is possible to administer these compounds to the animals continuously, as by constant feeding of a diet which contains one of the compounds, and thus assure that all parasites which contact the treated animal will be killed. Such administration is by no means economical, and it will usually be found best to administer the compounds at such times as to give the best return of parasite control for the compound expended. Certain parasites, such as cattle grubs, which are the larvae of the heel fly and the bomb fly, have a known active season when they attack animals. If such a parasite is of primary importance, the compounds can be used only during that season with assurance of year-round control of the parasite. Other parasites, such as ticks, infest and bite animals essentially the year round. Control of such parasites can still be accomplished with relatively brief periods of administration by administering the compound to all the animals on a farm or in an area for a short period of time, such as for a few weeks. All the parasites of a generation are thus killed, and the animals can be expected to remain parasite-free for a considerable length of time, for example until reinfested by parasites arriving with imported animals.

The compounds of formula I may be administered by any of the usual oral and percutaneous routes. It should be noted that many of the compounds are chemically changed by passage through the rumen of a ruminant animal. Oral administration to ruminant animals is therefore advisable only if the compounds are protected from the rumen environment by a special formulation. Such formulations will be discussed below.

The formulation and administration to animals of biologically-effective compounds is a very old and developed art. Some explanation of the different formulations and methods of administration will be given to enable all to practice parasite control using these compounds.

Percutaneous administration of formula I compounds is carried out in the ways usual in the animal veterinary art. It is convenient to use a water-soluble salt of the compound of formula I, such as the sodium salt, so that no elaborate formulation is required. On the other hand, if a water-insoluble compound is desired, it is practical to dissolve the compound in a physiologically-acceptable solvent, such as the polyethylene glycols. It is likewise practical to formulate an injectable suspension of the compound as a fine powder, suspended in a formulation of physiologically-acceptable nonsolvents, surfactants, and suspending agents.

The nonsolvent can be, for example, a vegetable oil such as peanut oil, corn oil, or sesame oil, a glycol such as a polyethylene glycol, or water, depending on the compound chosen.

Suitable physiologically-acceptable adjuvants are necessary to keep the compound of formula I suspended. The adjuvants can be chosen from among the emulsifiers, such as salts of dodecylbenzene sulfate and toluenesulfonate, ethylene oxide adducts of alkylphenol, and oleate and laurate esters, and from the dispersing agents such as salts of naphthalenesulfonate, lignin sulfonate and fatty alcohol sulfates. Thickeners such as carboxymethyl cellulose, polyvinylpyrrolidone, gelatin and the alginates are also used as adjuvants for injectable suspensions. Many classes of surfactants, as well as those which have been discussed above, serve to suspend the compound. For example, lecithin and the polyoxyethylene sorbitan esters are useful surfactants.

Percutaneous administration is conveniently accomplished by subcutaneous, dermal, intramuscular, and even intravenous injection of the injectable formulation. Conventional needle-type injection devices as well as needle-less air-blast injection devices are useful.

It is possible to delay or sustain the permeation of the compound of formula I through the animal's living tissues by proper formulation. For example, a very insoluble compound may be used. In that event, the slight solubility of the compound causes sustained action because the body fluids of the animal can dissolve only a small amount of the compound at any one time.

Sustained action of the compounds of formula I can also be obtained by formulating the compound in a matrix which will physically inhibit dissolution. The formulated matrix is injected into the body where it remains as a depot from which the compound slowly dissolves. Matrix formulations, now well known in the art, are formulated in waxy semisolids such as vegetable waxes and high molecular weight polyethylene glycols.

Even more effective sustained action is obtained by introducing into the animal an implant containing one of the compounds of formula I. Such implants are now well known in veterinary art, and are usually made of a silicone-containing rubber. The compound is dispersed through a solid rubber implant or is contained inside a hollow implant. Care must be taken to choose a compound which is soluble in the rubber from which the implant is made, since it is dispersed by first dissolving in the rubber, and then leaching out ot the rubber into the body fluids of the treated animal.

The rate at which the compound is released from an implant, and hence the length of time during which the implant remains effective, is controlled with good accuracy by the proper adjustment of the concentration of the compound in the implant, the external area of the implant, and the formulation of the polymer from which the implant is made.

Administration of the compounds by means of an implant is a particularly preferred embodiment. Such administration is highly economical and efficacious, because a properly designed implant maintains a constant concentration of the compound in the tissues of the host animal. An implant can be designed to supply compound for several months, and is easily inserted in the animal. No further handling of the animal or concern over the disage is necessary after the insertion of the implant.

Oral administration of a compound of formula I may be performed by mixing the compound in the animal's feed or drinking water, or by administering oral dosage forms such as drenches, tablets, or capsules.

When a compound of formula I is to be administered orally to a ruminant animal, it is necessary to protect the compound from the deleterious effect of the rumen processes. The veterinary art is now aware of effective methods for coating and encapsulating drugs to protect them from the rumen. For example, coating materials and methods are disclosed in Grant et al., U.S. Pat. No. 3,697,640. Grant teaches a method of protecting substances from action of the rumen by coating the substances with a film of cellulose propionate 3-morpholinobutyrate. Such a film can be used to protect the compounds of formula I. Conveniently, tablets, or capsules containing a compound of formula I are coated with the film in a coating pan or a fluidized bed spray apparatus. Pellets of the parasiticide may be made, coated with the film, and filled into capsules. Alternatively, a solid mixture of the compound and the film-forming agent may be made and broken or ground into small particles, each of which comprises the compound enclosed in a matrix of the film-forming agent. The particles may be filled into capsules for oral administration, or made into an oral suspension.

The formulation of veterinary additives in animal feed is an extremely well-known art. It is usual to formulate the compound first as a premix in which the compound of formula I is dispersed in a liquid or particulate solid carrier. The premix may conveniently contain from about 1 to 400 g. of compound per pound, depending on the desired concentration in the feed. As the art is aware, many compounds of formula I can be hydrolyzed or degraded by constituents of animal feed. Such compounds are routinely formulated in protective matrices such as gelatin before addition to the premix.

The premix is in turn formulated into feed by dispersing it in the feed mixture in a conventional mixer. The correct amount of compound, and hence of premix, to mix in the feed is easily computed by taking into account the weight of the animals, the approximate amount each animal eats per day, and the concentration of the compound in the premix.

Likewise, the amount of a compound to administer in the drinking water of animals is computed by taking into account the animal's weight and the amount each animal drinks per day. It is most convenient to use a water-soluble salt of a compound of formula I as a drinking water treatment. If such a salt is not desired, then a suspendable formulation of the desired compound must be made. The formulation may be a suspension in the concentrated form, which suspension is mixed into the drinking water, or may be a dry preparation which is mixed with and suspended in the drinking water. In either event, the compound must be in a finely-powdered form, and the formulation follows the same principles discussed above for injectable suspensions.

The compounds can easily be formulated into tablets and capsules according to the conventional methods, about which no teaching is required here. Drench formulations comprise the compound dissolved or dispersed in an aqueous liquid mixture. Again, it is most convenient to make the drench by dissolving a water-soluble salt of a compound of formula I. It is almost as convenient, however, and equally efficacious to use a dispersion of the compound made in the same way that the drinking water formulations discussed above are made.

The examples immediately below show the effectiveness of the compounds of formula I in controlling a number of parasites which normally affect economic animals. The compounds were tested against screwworms, which are larvae of the black blowfly, against the stable fly, against mosquitos, and against the adult American dog tick. The blowfly and stable fly are insects; the dog tick is representative of the acarina.

EXAMPLE 5

The stable fly is a common free-flying, bloodsucking parasite; the lone star tick is a typical bloodsucking parasite which spends the nymphal and part of the adult periods of the life cycle attached to the host animal, usually cattle. Blowfly larvae, or screwworms, hatch from eggs laid near a wound of the host animal by the free-flying insect. The larvae eat their way into the healthy flesh exposed by the wound and pass part of the life cycle therein, feeding on the host's flesh and blood.

The stable fly is parasitic on horses, mules, cattle, hogs, dogs, cats, sheep, goats, rabbits, and humans. The lone star tick is primarily a cattle parasite, but also attacks horses, mules, and sheep. Blowfly larvae attack any wounded animal, but are particularly harmful to cattle, hogs, horses, mules, sheep, and goats.

The following tests illustrate the efficacy of the compounds of formula I when they are administered to cattle. In most instances, the tests reported below were carried out on induced infestations of parasites.

A calf was treated with 15 mg./kg. of $N^1$-(2,2,3,3-tetrafluoropropionyl)-3'-nitro-5'-trifluoromethyl-o-phenylenediamine as a single subcutaneous injection. The compound was administered as a dispersion in 10 percent polyvinylpyrrolidone.

Adult stable flies were housed in chambers completely enclosed in wire screen. Two or more chambers, containing from 60 to 100 stable flies, were placed in contact with the clipped back of the calf 24 hours after administration of the compound. The flies were left to feed on the calf for the time indicated, after which the chambers were observed and the flies were left to feed for another time period. Chambers containing adult stable flies were placed in contact with the clipped back of an untreated calf to serve as controls. The mortality of the flies were determined by counting the number of live and dead flies after the exposure as compared to the control. Each set was run separately. The mortality results were as follows:

| Set | Hours Post-Treatment | Stable Fly Mortality % |
|---|---|---|
| 1 | 72 | 95 |
| 2 | 77 | 70 |
|   | 96 | 100 |
| 3 | 77 | 88 |
|   | 96 | 100 |
| 4 | 24 | 85 |
|   | 24 | 95 |

EXAMPLE 6

When the procedure of Example 5 was repeated using mosquitos, rather than stable flies, the result was:

| Set | Hours Post-Treatment | Mosquito Mortality % |
|---|---|---|
| 1 | 96 | 100 |

EXAMPLE 7

When the procedure of Example 5 was repeated using 25 mg./kg. in 10 percent polyvinylpyrrolidone, the results were:

| Set | Pest | Hours Post-Treatment | Mortality % |
|---|---|---|---|
| 1 | mosquito | 5 | 75 |
| 1 | mosquito | 24 | 100 |
| 2 | mosquito | 48 | 70 |
| 3 | American dog tick | 168 | 86 |

EXAMPLE 8

$N^1$-(2,2,3,3-tetrafluoropropionyl)-3'-nitro-5'-trifluoromethyl-o-phenylenediamine was tested at 10 mg./kg. in sesame oil against stable flies on a calf. The procedure was modified from the one described in Example 5 in that the wire chambers were placed on the back of the calf 24 hours after administration of the compound. The results are given in the following table:

| Time | Alive | Dead | Percent |
|---|---|---|---|
| Day 1 | | | |
| 6 hours | 20 | 20 | 50 |
| 24 hours | 0 | 40 | 100 |
| Day 2 | | | |
| 6 hours | 3 | 37 | 92 |
| 24 hours | 0 | 40 | 100 |
| Day 3 | | | |
| 6 hours | 16 | 24 | 60 |
| 24 hours | 4 | 36 | 90 |
| Day 4 | | | |
| 6 hours | 10 | 30 | 75 |
| 24 hours | 0 | 40 | 100 |
| Day 5 | | | |
| 6 hours | — | — | — |
| 24 hours | 0 | 40 | 100 |
| Day 6 | | | |
| 6 hours | — | — | — |
| 24 hours | 0 | 30 | 100 |
| Day 7 | | | |
| 6 hours | 3 | 37 | 93 |
| 24 hours | 6 | 34 | 85 |

-continued

| Time | Alive | Dead | Percent |
|---|---|---|---|
| Day 8 | | | |
| 6 hours | 35 | 5 | 12 |
| 24 hours | 15 | 25 | 62 |
| Day 9 | | | |
| 6 hours | 20 | 10 | 33 |
| 24 hours | 0 | 40 | 100 |
| Day 10 | | | |
| 6 hours | 40 | 0 | 0 |
| 24 hours | 40 | 0 | 0 |
| Day 11 | | | |
| 6 hours | 40 | 0 | 0 |
| 24 hours | 40 | 0 | 0 |

The tests reported immediately above demonstrate the long-lasting control of insect and acarina parasites which is obtained by the use of compounds of formula I. Administration of these compounds, even at quite low rates, has been shown to kill such parasites which feed on the treated animals even several days after administration of the compound. It is also notable that the control obtained was very complete, in that all, or essentially all, of the parasites which fed on the animal were killed.

The following procedure reports representative results of a bio-assay test.

Example 9

Larvae of the black blowfly were used as assay organisms in a bio-assay test system. The tests were carried out by administering a compound of this invention as a single subcutaneous injection to a calf. Samples of blood were withdrawn from the calf on successive days after the administration of the compound, and blowfly larvae were fed on the withdrawn whole blood. The end point of the test was recorded as the last day on which 90 percent or more of the blowfly larvae were killed. The results are given in the following table.

An additional in vitro test for evaluating the parasite control of adult stable flies by use of the compounds of formula I is described hereinbelow.

EXAMPLE 10

Eighteen hour starved adult stable flies were placed in a petri dish or fly cage and exposed to blood bait pads. The blood in the pads was collected from treated calves at designated time intervals, following treatment. Mortality of the stable flies was determined at designated time intervals after exposure to the blood bait pads. A percent mortality at these times was compared to the normal mortality obtained in petri dishes or fly cages containing blood from non-treated calves (control). The compound used in this test was $N^1$-(2,2,3,3-tetrafluoropropionyl)-3'-nitro-5'-trifluoromethyl-o-phenylenediamine. The results are given in the following table.

TABLE

| Dose (mg./kg.) | Blood Collected Hours Post-Treatment | Hours Observed Post-Contact with Blood | % Mortality |
|---|---|---|---|
| 15 in 10% poly-vinylpyrrolidone | 72 | 5 | 22 |
| | 72 | 24 | 89 |
| | 24 | 22 | 100 |
| 25 in dimethylsulfoxide | 2 | 18 | 100 |
| | 24 | 24 | 100 |
| 25 in 10% poly-vinylpyrrolidone | 168 | 24 | 92 |
| | 284 | 24 | 84 |
| 40 in 10% poly-vinylpyrrolidone | 312 | 24 | 100 |
| | 360 | 24 | 88 |

In the tests described above, the parasites were exposed to the treated animal's blood indirectly, instead of directly by feeding the parasites on the animal. The control obtained, however, is obviously as significant as if the parasites had sucked blood directly from the animal. The value in protecting animals from the very injurious parasite, the blowfly, is clearly demonstrated by the tests, since several days of parasite control were obtained from a single administration of a compound of formula I.

I claim:

1. A method of killing insect and acarina parasites which consume living tissues of a host animal which comprises orally or percutaneously administering to the host animal a parasiticidally-effective amount of a compound of the formula:

TABLE

| Compound | Solvent | Dose (mg./kg.) | Days Effective at 90 Percent or Greater |
|---|---|---|---|
| $N^1$-(2,2,3,3-tetra-fluoropropionyl)-3'-nitro-5'-trifluoro-methyl-o-phenylene-diamine | 10% polyvinyl-pyrrolidone | 40 | 25 |
| | | 25 | 18 |
| | | 15 | 11 |
| | | 10 | 8 |
| | | 5 | 6 |
| | | 2.5 | None |
| | sesame oil | 15 | 20 |
| | | 2.5 | None |
| | dimethylsulfoxide | 5 | 8 |
| | polyethylene glycol | 15 | 9 |
| $N^1$-chlorodifluoro-acetyl-3'-nitro-5'-trifluoromethyl-o-phenylenediamine | sesame oil | 15 | 8 |
| | 10% polyvinyl pyrrolidone | 20 | 8 |

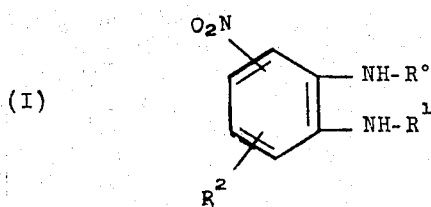

(I)

wherein
R° is a 2,2-difluoroalkanoyl radical of the formula

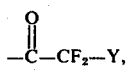

in which Y is hydrogen, chlorine, fluorine, difluoromethyl, perfluoroalkyl of $C_1$–$C_6$, or a radical of the formula

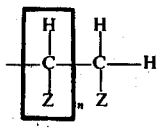

in which each Z independently is hydrogen or halogen and $n$ is 0 or 1;
$R^1$ is R°, hydrogen, a radical of the formula

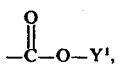

in which $Y^1$ is $C_1$–$C_4$ alkyl or phenyl, $C_1$–$C_8$ alkanoyl, benzoyl, furoyl, naphthoyl, or substituted benzoyl of the formula

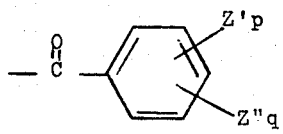

in which each Z' independently is halo or nitro, Z" is $C_1$–$C_4$ alkyl or $C_1$–$C_4$ alkoxy, $p$ is 0, 1, or 2, $q$ is 0 or 1, and the sum of $p$ and $q$ is 1–3;
$R^2$ is trifluoromethyl, difluoromethyl, or chlorodifluoromethyl, and the nitro group and $R^2$ are meta to one another; and
subject to the further limitation that where $R^1$ is hydrogen, the ring position ortho to the —NH—$R^1$ group bears one of the designated nitro or $R^2$ moieties.

2. The method of claim 1 in which the compound is of the formula

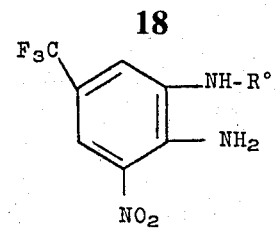

wherein R° is defined as in claim 1.

3. The method of claim 1 in which the compound is $N^1$-trifluoroacetyl-3'-nitro-5'-trifluoromethyl-o-phenylenediamine.

4. The method of claim 1 in which the compound is $N^1$-(2,2,3,3-tetrafluoropropionyl)-3'-nitro-5'-trifluoromethyl-o-phenylenediamine.

5. The method of claim 1 in which the compound is $N^1$-trifluoroacetyl-3'-trifluoromethyl-5'-nitro-o-phenylenediamine.

6. The method of claim 1 in which the compound is $N^1$-chlorodifluoroacetyl-3'-nitro-5'-trifluoromethyl-o-phenylenediamine.

7. The method of claim 1 in which the compound is $N^1$-trifluoroacetyl-$N^2$-benzoyl-6'-nitro-4'-trifluoromethyl-o-phenylenediamine.

8. The method of claim 1 in which the compound is $N^1$-trifluoroacetyl-$N^2$-naphthoyl-6'-nitro-4'-trifluoromethyl-o-phenylenediamine.

9. The method of claim 1 in which the compound is $N^1$-trifluoroacetyl-$N^2$-(p-n-butoxybenzoyl)-4'-trifluoromethyl-6'-nitro-o-phenylenediamine.

10. The method of claim 1 in which the compound is $N^1$-trifluoroacetyl-$N^2$-(p-nitrobenzoyl)-4'-trifluoromethyl-6'-nitro-o-phenylenediamine.

11. The method of claim 1 in which the compound is $N^1$-heptafluorobutyryl-3'-nitro-5'-trifluoromethyl-o-phenylenediamine.

12. The method of claim 1 in which the compound is $N^1$-pentafluoropropionyl-3'-nitro-5'-trifluoromethyl-o-phenylenediamine.

13. The method of claim 1 in which the compound is $N^1$-trifluoroacetyl-$N^2$-methoxycarbonyl-4'-trifluoromethyl-6'-nitro-o-phenylenediamine.

14. The method of claim 1 in which the compound is $N^1$-pentadecafluorooctanoyl-3'-nitro-5'-trifluoromethyl-o-phenylenediamine.

15. The method of claim 1 in which the compound is $N^1$-(2,2,3,3-tetrafluoropropionyl)-$N^2$-methoxycarbonyl-6'-nitro-4'-trifluoromethyl-o-phenylenediamine.

16. The method of claim 1 in which the compound is N-(pentafluoropropionyl)-3'-nitro-5'-trifluoromethyl-o-phenylenediamine.

17. The method of claim 1 in which from about 1 mg./kg. to about 100 mg./kg. of the compound is administered to the host animal.

18. The method of claim 17 in which from about 2.5 mg./kg. to about 50 mg./kg. of the compound is administered to the host animal.

19. The method of claim 17 in which the administration is percutaneous.

20. The method of claim 19 in which the compound is administered in an implant.

* * * * *